United States Patent [19]

Peterson

[11] Patent Number: 5,765,585
[45] Date of Patent: Jun. 16, 1998

[54] SAMPLE DECADE DILUTION SYSTEM AND PROCEDURE

[76] Inventor: Roger Peterson, Rte. 1 Box 316, Sweeny, Tex. 77480

[21] Appl. No.: 542,409

[22] Filed: Oct. 12, 1995

[51] Int. Cl.[6] .................................................. G05D 11/03
[52] U.S. Cl. .......................... 137/9; 137/599; 137/599.1; 137/605
[58] Field of Search ................................. 137/605, 606, 137/599.1, 9, 599

[56] References Cited

U.S. PATENT DOCUMENTS

| | | | |
|---|---|---|---|
| 3,830,256 | 8/1974 | Cox | 137/606 X |
| 3,886,971 | 6/1975 | Lundsgaard et al. | 137/606 X |
| 4,015,617 | 4/1977 | Connolly | 137/605 X |
| 5,052,425 | 10/1991 | Hohenberg et al. | 137/605 X |
| 5,261,452 | 11/1993 | McAndrew et al. | 137/606 |

*Primary Examiner*—Stephen M. Hepperle
*Attorney, Agent, or Firm*—Gunn & Associates, P.C.

[57] ABSTRACT

The method and apparatus of this disclosure are directed to a system for diluting a sample gas. For example, the sample gas may carry excessive water which creates difficulties in analysis. The apparatus includes an inlet line, a control valve which switches through several positions to provide 1, 2 or 3 decades of dilutions and each decade is defined by a flow through a restricted orifice calibrated to a specified flow volume. The sample is diluted with the dilution flow which is furnished through a similar orifice, but that orifice is replicated in a ratio of N:1. The N orifices provide the cumulative dilution flow which is commingle with the sample. Two more decades can be switched to obtain a wide range of dilution.

17 Claims, 4 Drawing Sheets

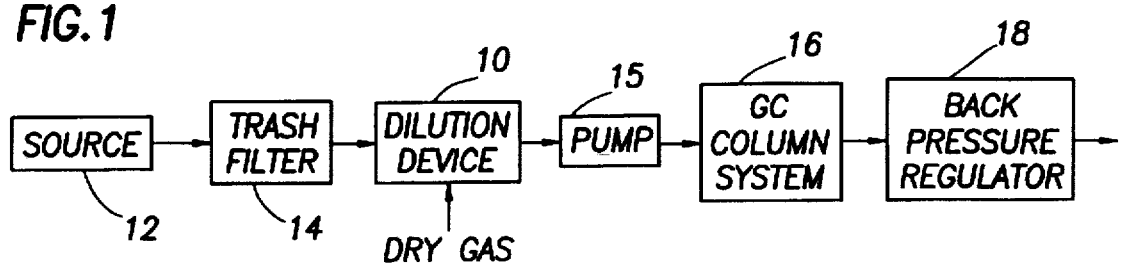
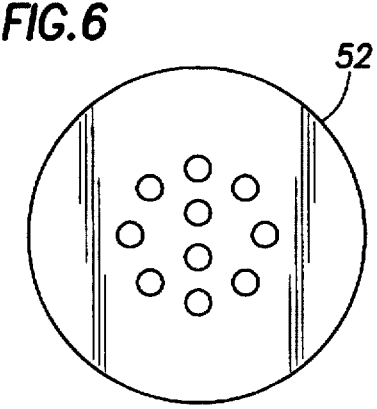
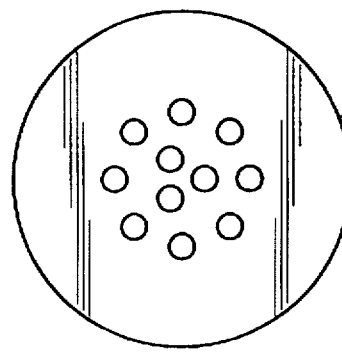
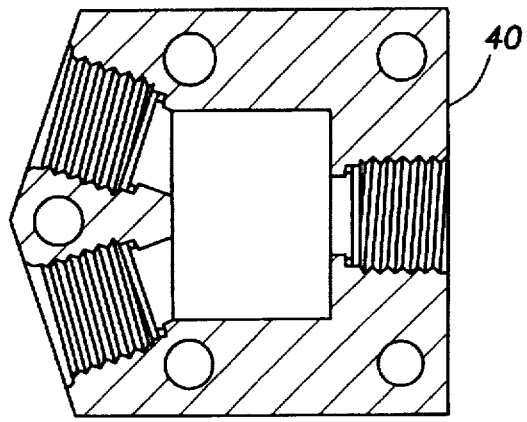
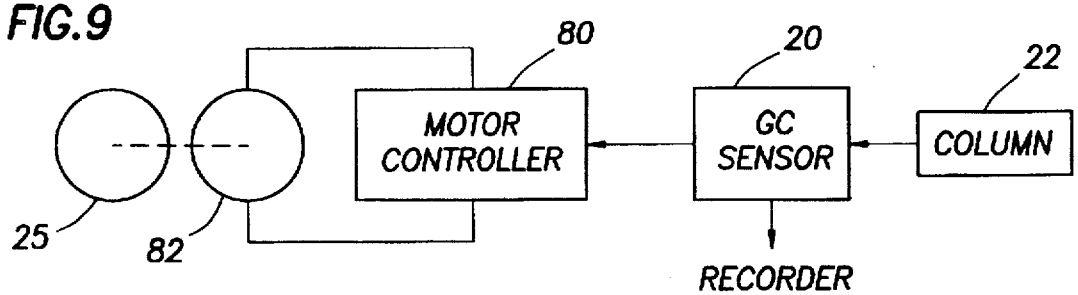

SAMPLE DECADE DILUTION SYSTEM AND PROCEDURE

BACKGROUND OF THE DISCLOSURE

The present disclosure sets forth a sample dilution technique which is especially useful in sample monitoring systems. It is sometimes necessary to monitor in a continuous mode of operation a gas source. Such a gas source can include, by way of example, a flow of air in the vicinity of a manufacturing process. The air is sampled to detect trace components flowing in the air which might create environmental difficulties in the near vicinity. As one example, this can occur in the immediate vicinity of a manufacturing system which combusts large quantities of hydrocarbon chemicals to make heat for the process. Such discharges are laden with products of combustion and also includes copious quantities of water of combustion. In an ideal situation, when a fuel is consumed, the products of combustion including primarily $CO_2$ and $H_2O$. In situations which are less than perfect, substantial quantities of fly ash and other particulate trash are also formed. In a more harmful aspect, some of the discharge components include such trace chemicals found in the fuel that the discharge may be laden with various derivatives from the trace constituents. A good example is sulfur in certain grades of coal or fuel oil. Sulfur, when converted in the combustion process typically forms $SO_x$, the most common being $SO_2$. $SO_3$ is also formed in some quantities. Such oxides as sulfides need to be monitored because they have a damaging impact when released atmosphere. One aspect of detecting the discharged materials is that it is mixed with the particulate trash and water. Indeed, the relative humidity in the flue typically approaches 100%. This is especially true where the furnace combusting such products discharges the flue gases to atmosphere through a relatively tall chimney. There will be cooling of these gases as they rise in the chimney. With cooling, the humidity is always 100%. Indeed, some of the water may form droplets. Such droplets will collect on the sidewall of the chimney.

Such droplets will also dissolve oxides of sulfur, pick up the flash, and cause a very undesirable liquid spattering. In that context, a sample must be periodically obtained, perhaps even continuously, to monitor the performance of the system.

The present disclosure sets forth a monitoring system which is useful in the foregoing context. It deals with the excessive humidity and trash which is carried in the flowing stream. Where an excess humidity is encountered, there is a tendency of the very humid air which is being sampled to cause wet slurry coagulation in the sampling equipment. Samples ordinarily do not require copious quantities of the input gas. Indeed, the sampling equipment normally works on a very small flow. As the sample flow becomes smaller, the risk or susceptibility to plugging is greater in that a smaller orifice is exposed to plugging. When that plugging might occur, the test equipment is then handicapped. One cure of that is to take in more sample and operate a larger system. The detrimental side of that is directly tied to the detrimental impact of the oxides of sulfur along with the water droplets which may condense should the humidity approach 100%.

The disclosed system of the present disclosure enables sampling of an air source which is exposed to 100% humidity. In the foregoing example, identified flue gases from a furnace cause the same problem in ambient air in a large number of manufacturing plants around the country. Such plants are typically constructed near a body of water for ocean going transportation. Barge traffic up and down rivers or along the coast is essential for operation. It is therefore quite common that the ambient air is typically at 50% humidity, but often ranges as high as 90 or 95% humidity. This is especially true for the petrochemical complex scattered along the Gulf Coast. While the source of the humidity is different in this instance, it poses something of the same problem. Even the sampling of ambient air without ash and without the other components that are typically of a flue gas discharge, it is not easily done.

As will be understood, continuous monitoring requires a system that will not plug or otherwise be handicapped in its operation. Continuous monitoring also requires that the system cycle and recycle copious quantities of the ambient air being sampled where the system is able to provide a suitable scaled output.

Chemical test apparatus now operates with a sensitivity that is extremely delicate. It is not uncommon for systems to be able to respond to one part per million or even one part per billion. In operating at this sensitivity, the flue gas discharge may be excessive in that the sample will overdrive the system. For instance, if a system can provide a full scale output from the sensor at one part per million of a trace constituent, it ill suits the system to overdose the sensor with a sample which is perhaps 100 times stronger. It is desirable to avoid overloading or saturating the sensor. To accomplish this, sample dilution is used in the present system to bring the sample into a range which is customarily encountered by the test sensor. Further, the sensitivity requirements, and the risk of overdosing with excessive water vapor creates something of a set of differing demands on the system. Since these demands derive from scaling needs which are not necessarily the same, it is important to sometimes change the sensitivity of an instrument. The present invention represents a scaling system which enables a decade dilution factor to be incorporated and adjusted from time to time. When that occurs, it can be adjusted so that the sample has sufficient strength that the sample input into the sensor provides a robust sensor signal. In like fashion, it is diluted so that water from the humidity in the air does not provide a serious problem to the operation of the system.

SUMMARY OF THE INVENTION

Coming now therefore to the present system, it is summarized as a constant pressure decade dilution system utilizing a restricted passage in a short tube. The restricted passage in a short tube provides a constant through put. A source of dry inert gas or air is used for dilution. The dry gas is diluted with the sample gas in a specified ratio which is 10:1, the apparatus providing a single tube for the sample and 10 tubes for the dilution gas. This equipment is replicated in conjunction with the control valve to enable provision of dilution steps of 1:1, 10:1, 100:1, etc. Typically, four decades of dilution are sufficient. Further, this enables the device to be controlled at its location or remotely for proper dilution of the air born sample undergoing test. As will be appreciated, other sample sources can be used.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a schematic block diagram of the sample decade dilution system of the present disclosure;

FIGS. 6 and 7 are sectional views showing a fitting supporting 10 and 11 restrictor tubes respectively;

FIG. 8 is a sectional view through a mixing system enabling the dilution of the sample in a controlled quantity;

FIG. 9 is a partial schematic showing a mechanism for switching the dilution ratio.

DESCRIPTION OF THE PREFERRED EMBODIMENT

Figure 2:
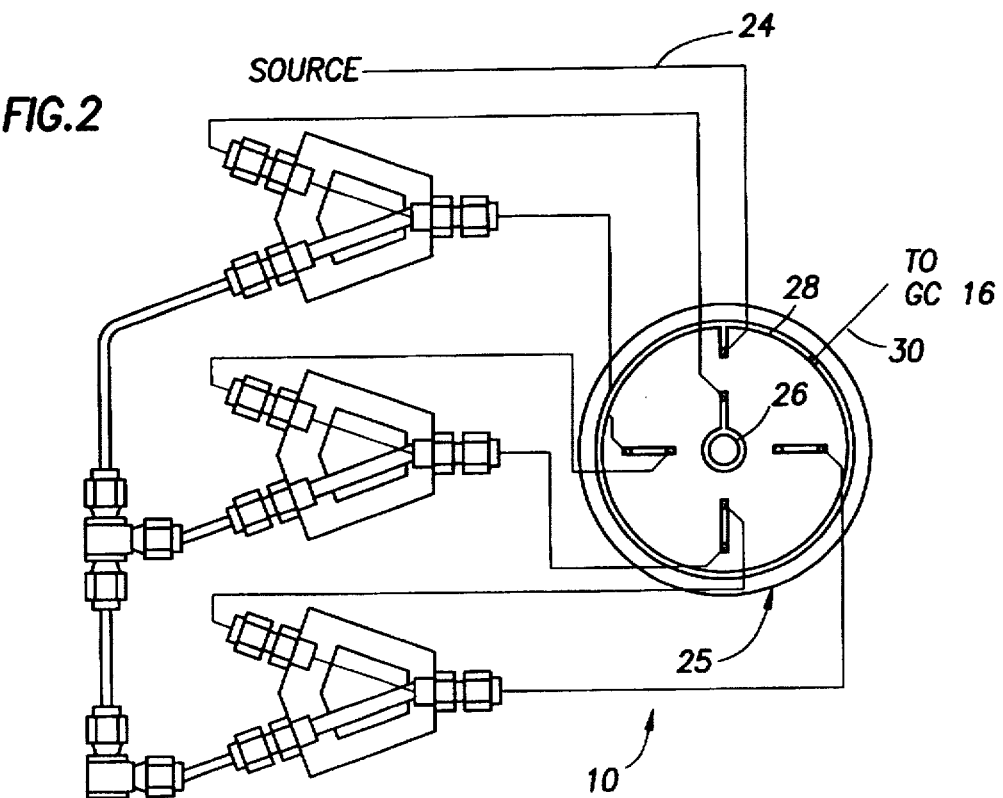
FIGS. 2, 3, 4, and 5 show the decade dilution of the present disclosure at different switch positions to provide different dilution ratios.

Attention is now directed to FIG. 1 of the drawings which shows the system in block diagram form. FIG. 1 provides the context for understanding the sample dilution system of the present disclosure and then particularly the point of installation in a process sampling system. Thus, FIG. 1 shows the dilution device 10 installed in a system. To make it more readily understood, the system of FIG. 1 will be described first. In that view, a source 12 provides a gas flow which is susceptible to excessive humidity or particulate trash. The source 12 was exemplified in the background given above. Suffice it to say, the source can be as simple as an intake installed in a chimney. It may be more sophisticated depending on the requirements of the installation. In any event, a source is collected and input in a continuous flow to a trash filter 14. The filter is incorporated to remove particles which might otherwise plug the operation of the remaining equipment. This is sometimes deleted because there are no gas carried particles that pose a problem. On the other hand, they are typically encountered in combustion discharges. After particulate filtration, the flow is then through the dilution device 10 of the present disclosure. That is operated by exposure to a constant pressure which is provided by a pump 15. The pump 15 delivers under pressure the diluted sample to a GC system 16. That is operated with a fixed back pressure regulator 18. This enables the GC system to operate with a constant pressure across it. In like fashion, the dilution device 10 of the present disclosure is presently operated with a fixed pressure differential across it. This enables the system to operate without variation derived from pressure variations inflicted on the system.

Typically, the output of the system is a signal curve from the GC system 16. More specifically, the output is typically obtained from a GC sensor. Going momentarily to FIG. 9 of the drawings, it shows a GC sensor 20 which is provided with a peak separation from the GC column 22. The GC sensor forms an output signal which is applied to a recorder or other equipment. That sensor may have a sensitivity which provides a full scale signal even when the sample of interest has only one part per million of the gas of interest. The GC sensor can be, by way of example, a flame ionization detector. Other sampling devices are also known. Representative full scale values can be provided by a variety of sensors with trace samples having concentrations as small as $10^7:1$.

In the foregoing, it is assumed (1) that the sample flow is provided at a relatively fixed flow rate such as 100 to 200 cc per minute, (2) that it is exposed to up to 100% humidity (from the water and the sample) and (3) that it is delivered at a relatively fixed pressure into the dilution device 10 operating with a fixed flow rate and a relatively controlled back pressure arrangement.

DECADE DILUTION CONTROL VALVE

Attention is now directed to FIG. 2 of the drawings. The trash filter 14 shown in FIG. 1 provides an outlet flow which is input through the line 24. It is delivered to a decade selector valve 25. This valve has 4 positions but it will be understood that it can be 2, 3, 4 or more positions. After a full description of the operation of the four similar views, decade switching will be understood in the context. The valve 25 has an inlet port connected to the line 24 and a rotor 26. The rotor is shown in FIG. 2 of the drawings switched to a position so that no dilution occurs. The rotor 26 makes the needed connections so that the line 24 is input to the flow path 28 which includes the port 30 which extends to the GC 16. As will be understood, the rotor is able to connect the internal passage 28 with the port 30. When that connection is accomplished, the source line 24 is connected directly to the GC system downstream. In other words, the connection as just described provides a 1:1 proportioning of the input flow. There is no dilution in this instance.

Figure 3:
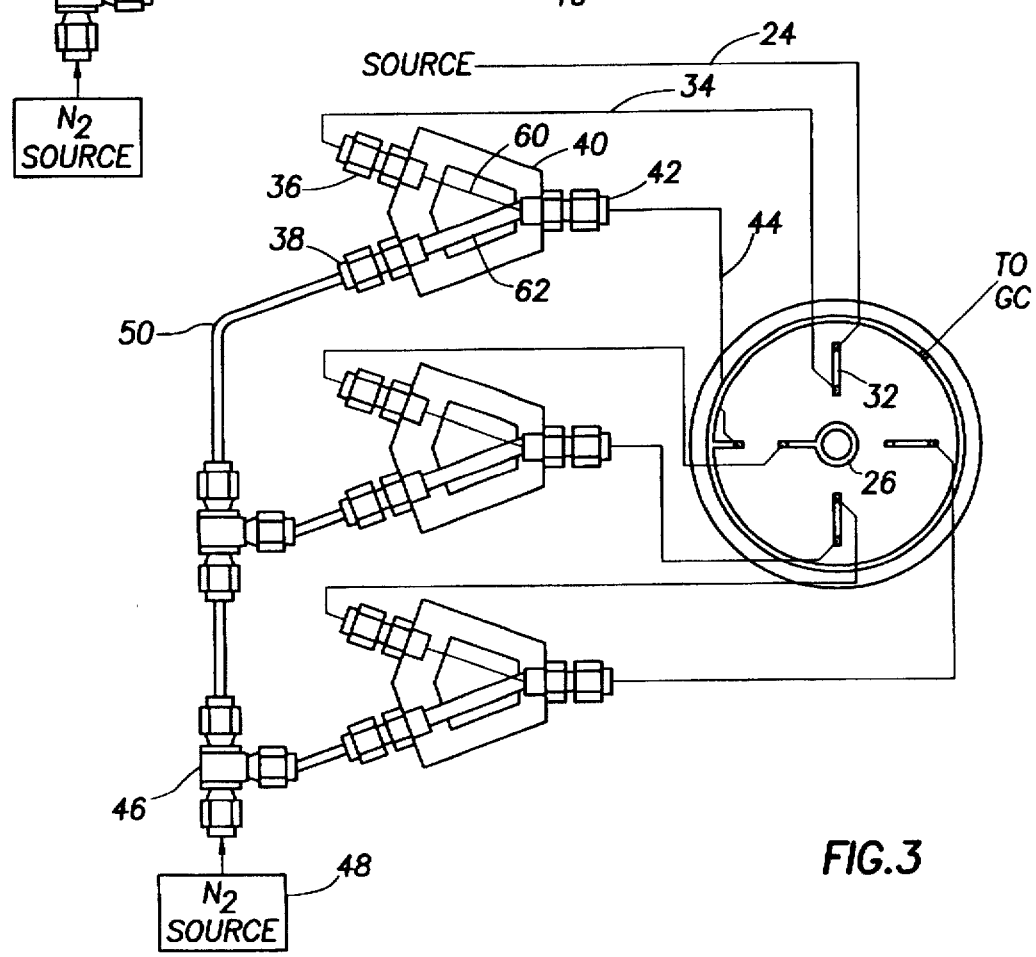

FIGS. 2, 3, 4 and 5 show the same structure with switching that is accomplished in the valve 25. Attention is now directed to FIG. 3 of those drawings realizing that it is the same structurally in all regards. FIG. 3 differs however in rotation of the rotor 26. When this rotation occurs, different switching is accomplished by the valve 25. For purposes of description, FIG. 3 will be described as providing only one decade of dilution. In other words, it provides a reduction of 10:1.

Going therefore with FIG. 3 of the drawings, the source line 24 is again illustrated. The rotor 26 operates so that the source line 24 is connected by a rotor passage 32 with a line 34. This line 34 is connected with a suitable tubing fitting 36. A similar fitting 38 is likewise included from a dry inert gas source to be described. The fittings 36 and 38 are supported on a decade tube support 40. The output of the decade tube support is through a fitting 42 input to a line 44. The line 44 connects with the valve 25 and is connected after switching to the internal passage 28 and is then output through the port 30.

FIG. 3 shows a tee 46 which is input from a mixing gas source 48. The preferred embodiment utilizes dry nitrogen air. Other dry sources can be used including air. The primary criteria is that it be free of water and particles. The nitrogen source 48 is connected through a line 50 which is input through the fitting 38 previously mentioned. The fitting 36 is input to the decade dilution support 40. Briefly, a thin small feed line is connected with the fitting 36. Only one such line is used. The fitting 38 supports 10 such lines. In the aggregate, 11 lines are connected to the fitting 42. These are relatively small lines. These small lines add cumulatively at the fitting 42 and provide an output through the line 44 to the valve 25.

Attention is momentarily diverted to FIGS. 6, 7 and 8 considered jointly. The support 40 is shown in FIG. 8 of the drawings with drilled passages which are internally tapped with threads to form a seal with the fittings 36 and 38. The fitting 38 is closed by a captured plate 52 and it is provided with 10 drilled holes. The plate 54 shown in FIG. 7 has 11 drilled holes. The plates are identical in all aspects other than the number of drilled holes. Even in that aspect, the drilled holes are located in approximately the same pattern. Going back to FIG. 3 of the drawings, the numeral 60 identifies a single relatively small feed line. A single line of specified diameter is included at 60 while 10 such lines are included at 62. The 10 lines 62 connect between the plates 52 and 54. They fill the 10 openings in the plate 52 and they connect with 10 of the 11 openings in the plate 54.

The tube 60 is quite small. It is replicated by the tubes 62. They differ only in their point of installation. In the preferred embodiment, the tube 60 is about one or 2 inches in length. More important than length, the tube is provided with a narrow internal passage. Even though the tube 60 may be cut from a well made spool of tubing and even though perfectly cuts are made at both ends of the tubing segments, the flow or throughput of a given tube may vary slightly. By means well-known and using calibration techniques well-known, it is possible to measure the flow or throughput of a given tube. So to speak, the tube functions as a restrictive orifice in a flow plate. Again, calibration for an orifice in a flow plate is believed to be well-known. Trimming or adjustment of the flow can be achieved quite easily and simply by crimping the tube some place along its length. This typically requires that the tube be slightly squeezed with a hand tool such as pliers or the like. When squeezed, the crimp formed in the tube will restrict the flow through the tube. When squeezed, adjustments are then made in the flow so that the desired flow rate can then be obtained.

The individual tube 60 is installed in the mounting plates 52 and 54. As will be understood, the fitting 36 supports a plate like the plate 52 except that it has only a single hole in it. The plates are installed and sealed along the outer periphery. The tubes 60 and 62 are likewise sealed around the edge at the connective hole. In other words, they are sealed to prevent leakage around the holes in the plates 52 and 54. The sole and exclusive flow path is through the tubes 60 and 62.

All the tubes are calibrated to the same flow rate. If that is done, the structure shown in FIG. 3 and as described in this juncture is thus constructed and arranged to provide a 10:1 dilution. One unit of gas is introduced through the tube 60 while 10 units of gas are introduced through the several tubes 62. Since there are 10 tubes in that bundle, the ratio of 10:1 is accomplished. The flow from the fitting 42 is the flow of the sample which has been diluted by 10 fold or provides an output of 10:1.

Figure 4:
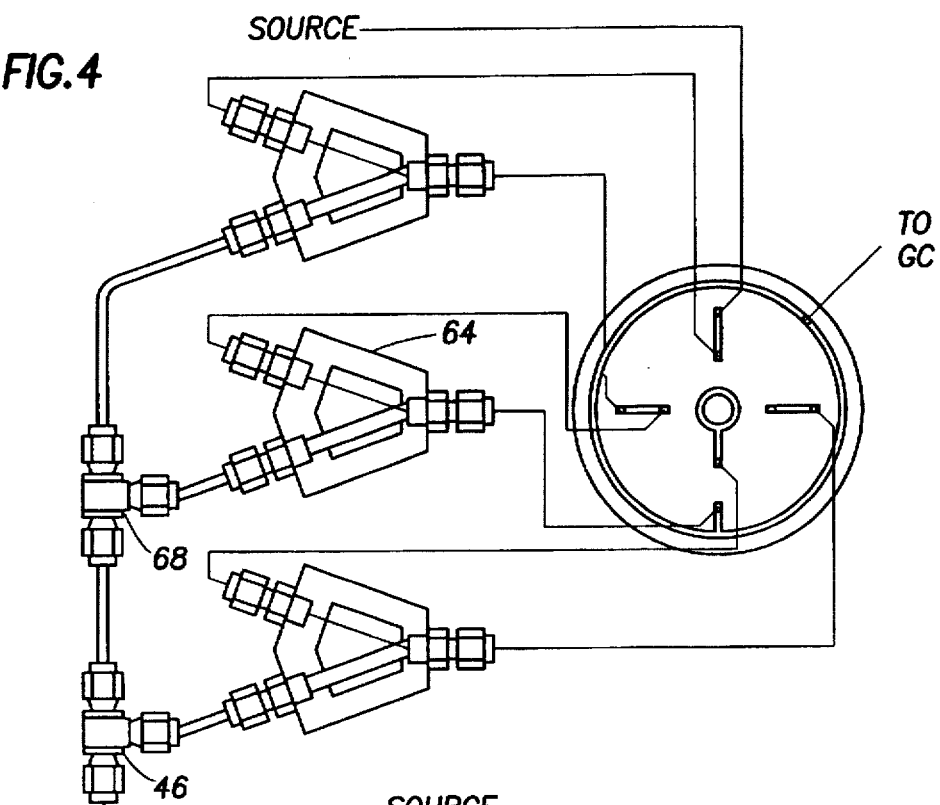
Figure 5:
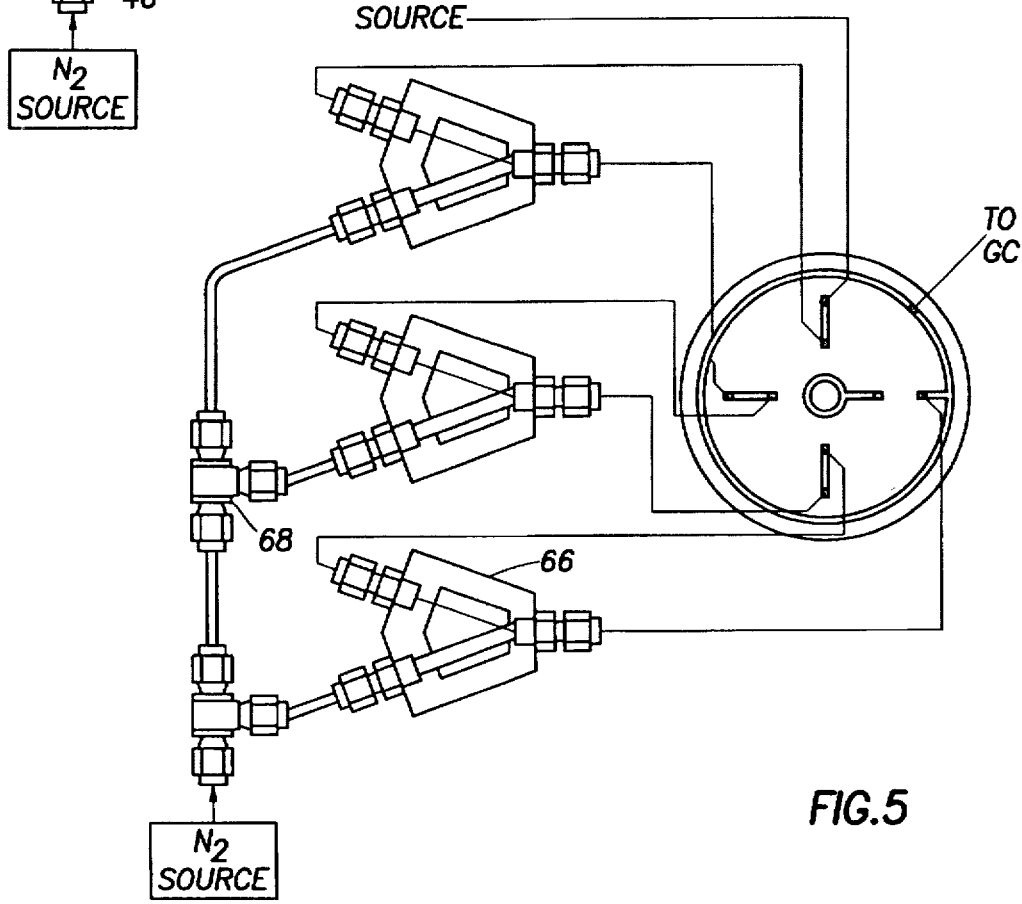

Attention is now directed to FIG. 4 of the drawings. In FIG. 4, another decade dilution support 64 is incorporated. In FIG. 5 another support 66 is incorporated. The dilution supports 64 and 66 are identical; they add additional decades in the system. For that reason, it is believed that a detailed description is not required. It is however noted that, in FIGS. 4 and 5, the nitrogen source 48 connects with the tee 46 previously identified and a serial tee 68. The serial tee 68 provides flow for the decade dilution support 64 while the tee 46 diverts nitrogen flow for the support 66.

Considering FIGS. 2, 3, 4 and 5 collectively, they show a decade dilution system capable of providing a thousand fold change in dilution. This can be extended another two or three decades if desired.

An important aspect of the present apparatus is that it works with a substantially constant pressure differential across the dilution device 10. This is added by the use of the pump 15. Indeed, it may be appropriate to place an upstream pump in front of the dilution device, and install an additional pump downstream. Alternately, a back pressure regulator can be used downstream. An important aspect of operation derived from this fact is that the pressure at the dilution device 10 is held steady or constant. It is also desirable that the input sample flow from the source be provided by filtration of the source gas. Moreover, this enables the dilution device to provide the controlled decade steps in operation that enable dilution in the control fashion.

In some instances, it is desirable to cooperate with digital equipment which operates on a pure binary basis. In that instance, it might be helpful to provide a dilution ratio of 8:1 at each stage. With several serially arranged stages, this can provide dilution ratios of 8:1, 64:1, 512:1, 1024:1, etc. As will be understood, the foregoing arrangement provides output sample dilution in ratios that lend themselves readily to cooperative digital equipment.

The GC system in actuality includes several components but the two major components are the GC itself and also the output sensor or detector. There are many various different GC detectors. Without belaboring the point, FIG. 9 of the drawings illustrates a GC sensor which forms an output signal for a recorder. To the extent that the GC sensor is provided with a signal at the time of calibration which is too small or too large, FIG. 9 shows a modification which enhances this. If the signal does not achieve a requisite threshold, there is excessive dilution. On the other hand, if the signal is driven to the limits, then the concentration is too great. In either instance, it may be desirable to adjust the dilution ratio. A motor controller 80 is incorporated for this purpose. The motor controller 80 drives a stepping motor 82 to rotate, thereby rotating the valve 25. The valve 25 is rotated in 90° steps as illustrated in FIGS. 2, 3, 4 and 5. With 90° of rotation, stepping moves the system to operate by a different dilution ratio changing by 10 fold. If that is done, the sample provided to the GC sensor 20 will be changed in relative ratio. This enables periodic adjustment. This enables proper sizing of the sample so that the sensor can provide an output in the most desirable operative range, i.e. a range in which the output signal is maintained between selected upper and lower limits for operation of the sensor 20. Ideally, this is switched under control of the operator when in manual operation, and is occasionally changed by the operator to achieve a specified dilution ratio.

The device of the present disclosure is relatively small. It can be made with the valve 25 and three of the decade dilution supports 40, 64 and 66 packaged in a single structure which is quite small. If need be, the motor 82 can be replaced with a hand control switch and the motor itself and the motor controller can be packaged integral with the structure without substantial increase in size. The tubing and fitting shown in the views is relatively small also. As noted, the tubing 60 is quite small, typically having an ID that is in the range of 1/16 inch, and typically much smaller. Tubing which is 1/32 inch OD has been found acceptable.

Figure 10:
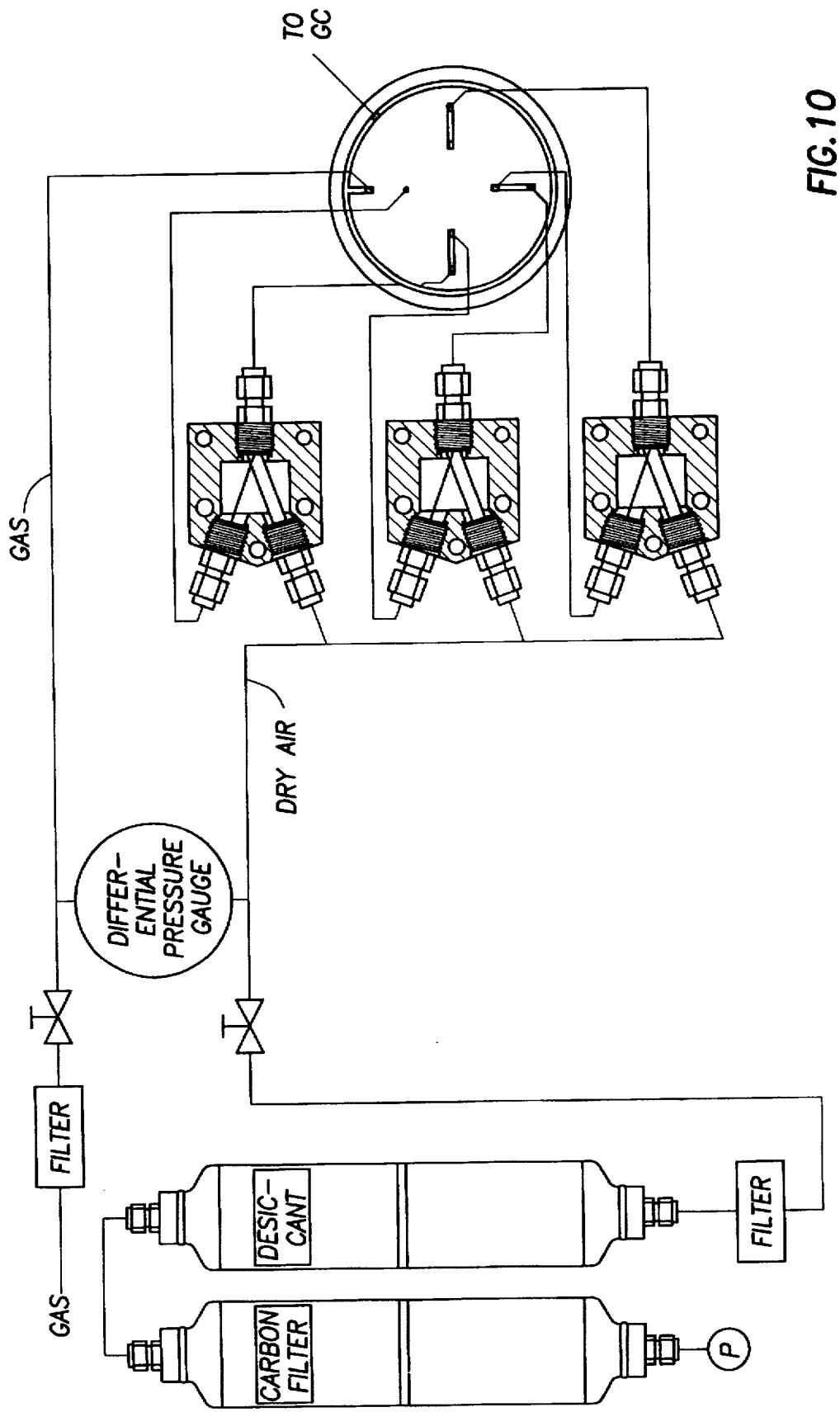
FIG. 10 shows an air dilution source for the present sample decade dilution system.

FIG. 10 shows an alternate to a nitrogen system. Air is taken in through two filters including a carbon filter and desiccant (water removing) filter. This furnishes dry air for dilution. A pump can be used to drive the system.

While the foregoing is directed to the preferred embodiment the scope thereof is dependent on the claims which follows.

What is claimed is:

1. For use with a sample source providing a sample to be tested in a test instrument or the sample is subsequently diluted prior to testing in the sample sensor for forming an output from the sample sensor indicative of sample concentration, a dilution system which comprises:

(a) a sample source supply line connected to valve system for input thereto and said sample line provides a sample flow at a regulated and controlled quantity;

(b) a source of diluent gas for mixing with the sample;

(c) a restrictive orifice controlling the flow of the sample through said orifice;

(d) a restrictive orifice restricting the flow of the diluent, wherein said restrictive orifice is replicated so that the flow of the diluent is proportioned in a desired ratio with respect to the flow of the sample and that ratio is represented by the ratio of N:1 where N is a specified positive integer; and (e) an outlet line connected with said valve system to receive the flow of the sample and the diluent wherein the flow in the outlet line is mixed so that the diluent provides a dilute sample in the ratio of N:1 and said line is connected through said valve system so that the diluent flow in tile outlet line is directed to a sample test apparatus, wherein (f) said sample source supply line connects to a source of water laden sample and the water laden sample is diluted with dry diluent to a ratio of N:1, and said outlet provides through said valve system the diluted flow;

(g) said valve system controllably switches to change the dilution ratio from 1:1 to N:1; and (h) said valve system also switches to change the dilution ratio to $N^2:1$ by connecting a second set of said restrictive orifice and diluent restrictive orifices serially so that said second set dilutes the flow from said outlet line.

2. For use in a sample dilution system capable of forming a sample diluted in a ratio of N:1, where N is a whole number positive integer, an apparatus comprising:

(a) a dilution support having three ports therein and wherein:

(1) said first port incorporates a fitting for connection with a source of sample;

(2) wherein said second port incorporates a fitting connected to a source of dilution material having the same phase as the sample;

(3) and wherein said third port is connected to said first port to deliver the flowing diluted sample therefrom;

(b) a restrictive orifice associated with the first port to limit the rate of flow of the sample through said first port; and (c) multiple restrictive orifices provided in a ratio of N:1 wherein N orifices each admit separately the sample and diluent to enable flow for commingling with the sample input through the sample port; and further wherein said support directs flow into said outlet port thereof, wherein (d) said dilution support is controllably switched into operation by a control valve system to change the dilution from no dilution to dilution or a ratio of N:1;

(e) said control valve system switches serially a second dilution support at a ratio of N:1 to provide control valve system controlled dilution at ratios of 1:1, N:1 and $N^2:1$; and (f) said control valve system switches serially a third dilution support into operation to provide controlled dilution ratios at 1:1, N:1, $N^2:1$ and also $N^3:1$.

3. The system of claim 2 wherein said one or more restrictive sample orifices and said restrictive diluent orifices are formed from a set of cut tubes wherein each of said tubes is calibrated to the same flow rate to provide said fixed flow rate ratio at N:1.

4. The system of claim 2 wherein said sample source supply line connects to a source of water laden sample and the water laden sample is diluted with dry diluent to a ratio of N:1, and said outlet provides through said valve system the diluted flow.

5. The system of claim 4 wherein said valve system controllably switches to change the dilution ratio from 1:1 to N:1.

6. The system of claim 2 wherein said dilution support is controllably switched into operation by a control valve system to change the dilution from no dilution to dilution or a ratio of N:1.

7. The system of claim 6 wherein said control valve system switches serially a second dilution support at a ratio of N:1 to provide control valve system controlled dilution at ratios of 1:1, N:1 and $N^2:1$.

8. The system of claim 2 wherein said system operates under control of a sample pump so that system pressure is held relatively steady.

9. A method of mixing a dilution material of the same phase as a sample wherein the sample is input through a sample source, the method comprising:

(a) introducing a sample from a source for mixing with a dilution flow wherein the dilution flow is metered through N flow orifices wherein the orifices provide an aggregate total flow so that dilution is accomplished in the ratio of N:1 where N is a whole number positive integer;

(b) controlling the pressure of the sample flow and the dilution flow;

(c) delivering the sample flow through an orifice;

(d) mixing the sample flow with the dilution flow after metering so that the mixed flows are directed through N+1 orifices;

(e) directing the flow after mixing into a delivery line; and (f) controlling the pressure differential across said N+1 orifices.

10. The method of claim 9 including the step of taking an air sample subject to 100% humidity, diluting the sample with dry gas to ratio of N:1 with the dry gas and reducing the air sample humidity to 100%/N.

11. The method of claim 10 including the step of obtaining the dry gas by flowing air through a filter and drying the air.

12. The method of claim 9 including the step of metering sample gas flow through the orifice; mixing the dilution flow metered through the N flow orifices with the sample gas source; and also calibrating the orifices to a selected gas low rate;

after mixing, further diluting the diluted sample gas flow with dilution gas flow from the same source, thereby providing a sample gas flow diluted by N and by a second ratio.

13. The method of claim 9 including the step of diluting gas into the sample gas flow at least three times to firm a sample gas flow diluted by N from a first, second and third set of orifices.

14. The method of claim 13 wherein the dilution is given by $1/N_1 \times N_2 \times N_3$ where $N_1$, $N_2$ and $N_3$ are ratios defined by first, second and third sets of orifices.

15. The method of claim 9 including the preliminary step of forming dry dilution air by filtering and drying ambient air;

then mixing the filters and dried air with the sample gas flow;

diluting and mixing the gas sample serially first and second times.

16. The method of claim 15 including the post mixing step of mixing with a second dilution flow and then mixing with a third dilution flow to dilute the sample gas by a specified amount and then stopping the step of mixing the third dilution flow.

17. The method of claim 16 including stepping a rotatable valve through at least two positions so that mixing the third dilution flow is turned on and off thereby.

* * * * *